United States Patent
Pauker et al.

(12)
(10) Patent No.: US 6,554,793 B1
(45) Date of Patent: Apr. 29, 2003

(54) FLEXIBLE TROCAR WITH AN UPTURNING TUBE SYSTEM

(75) Inventors: Fritz Pauker, Wiffertshausen/Freidberg (DE); Thomas Viehbach, Pischertshofen (DE); Robert Pauker, Kissing (DE); Gerhard Weiglhofer, Schwabhausen (DE)

(73) Assignee: STM Medizintechnik Starnberg GmbH, Schwabhausen/Weil (DE)

( * ) Notice: Subject to any disclaimer, the term of this patent is extended or adjusted under 35 U.S.C. 154(b) by 0 days.

(21) Appl. No.: 09/445,534

(22) PCT Filed: Apr. 7, 1999

(86) PCT No.: PCT/EP99/02476

§ 371 (c)(1),
(2), (4) Date: Feb. 23, 2000

(87) PCT Pub. No.: WO99/51283

PCT Pub. Date: Oct. 14, 1999

(30) Foreign Application Priority Data

Apr. 7, 1998 (DE) ........................................ 198 15 598

(51) Int. Cl.$^7$ ............................................ A61M 37/00
(52) U.S. Cl. .................................. 604/95.01; 604/158
(58) Field of Search .......................... 604/95.01, 95.02, 604/95.03, 95.04, 95.05, 264, 164.01, 158

(56) References Cited

U.S. PATENT DOCUMENTS

| | | | | |
|---|---|---|---|---|
| 3,470,876 A | * | 10/1969 | Barchilon | 604/95.04 |
| 4,366,810 A | | 1/1983 | Slanetz, Jr. | 128/6 |
| 4,753,223 A | * | 6/1988 | Bremer | 128/4 |
| 4,841,949 A | | 6/1989 | Shimitzu et al. | 128/4 |
| 5,108,368 A | * | 4/1992 | Hammerslag et al. | 604/95 |
| 5,176,126 A | * | 1/1993 | Chikama | 128/4 |
| 5,179,935 A | | 1/1993 | Miyagi | 128/4 |
| 5,209,741 A | * | 5/1993 | Spaeth | 604/264 |
| 5,325,845 A | * | 7/1994 | Adair | 128/4 |
| 5,683,413 A | | 11/1997 | MIyagi | 606/205 |
| 6,007,531 A | * | 12/1999 | Snoke et al. | 606/15 |

FOREIGN PATENT DOCUMENTS

| | | | | |
|---|---|---|---|---|
| DE | 28 20 239 A1 | 11/1978 | | A61M/25/00 |
| DE | 42 22 121 C1 | 9/1993 | | B25J/18/06 |
| WO | WO 93/13704 | 7/1993 | | A61B/1/00 |

* cited by examiner

*Primary Examiner*—Manuel Mendez
(74) *Attorney, Agent, or Firm*—William W. Jones

(57) ABSTRACT

A flexible trocar assembly includes an inner flexible tube and a concentric outer flexible tube. The flexible tubes are spaced apart from each other so as to form an open ended annular space in the trocar assembly. The annular space contains surgical instrumentation and passages for inflation gases, trocar assembly rigidifying gases or materials, and trocar manipulating mechanisms. For example, fiber optic light transmitters associated with camera-related fiber optics can be disposed in the annular space so that an area in a body cavity being examined can be illuminated and observed. Trocar manipulating mechanisms such as Bowden cables can also be disposed in the annular space. Liquid flushing tubes can be positioned in the annular space. Carbon dioxide or air injecting tubes can be positioned in the annular space. The inner flexible tube defines a central trocar assembly passage through which surgical instruments can be inserted into the body cavity. The trocar assembly is particularly useful in performing surgical procedures in the colon. An invertable tube assembly is associated with the trocar assembly and is used to move the trocar assembly into and out of the body cavity. The invertible tube embraces the trocar assembly and the invertible tube is moved forward and backward by a controlled drive mechanism. Lubrication is provided between the invertible tube and the trocar assembly so as to reduce friction between the invertible tube drive mechanism and the trocar assembly.

9 Claims, 9 Drawing Sheets

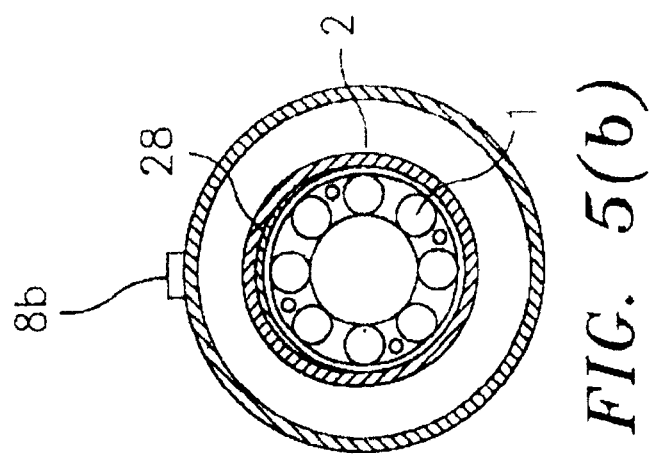
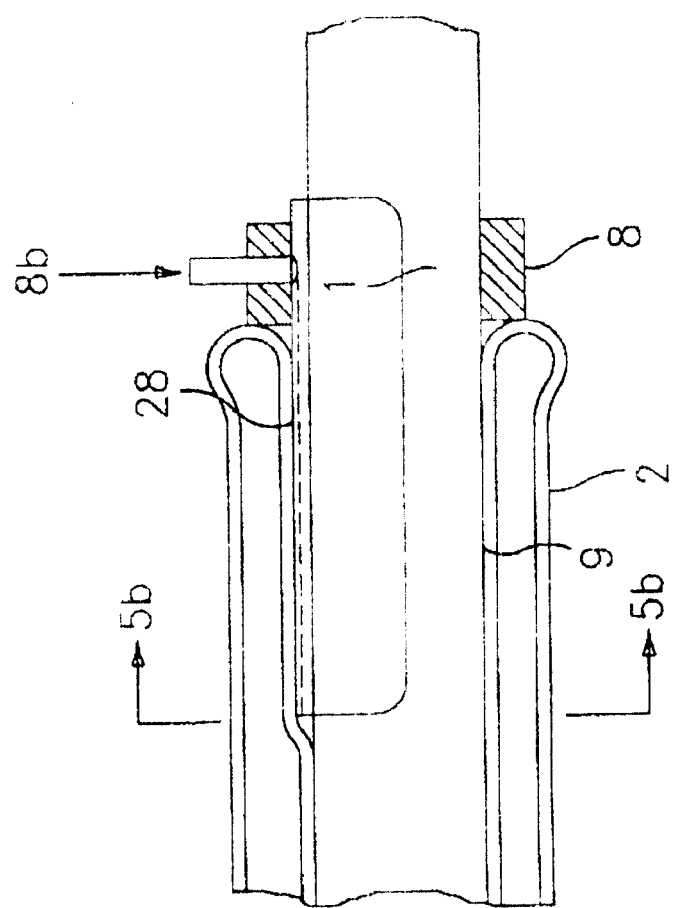
FIG. 5(b)
FIG. 5(a)

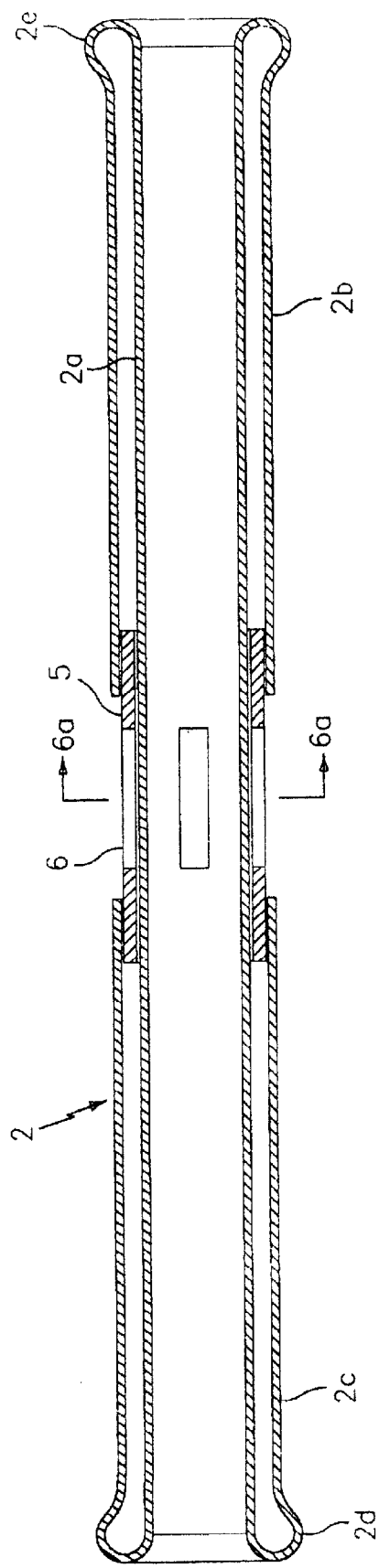
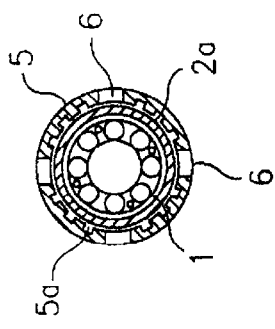
FIG. 6
FIG. 6(a)

FLEXIBLE TROCAR WITH AN UPTURNING TUBE SYSTEM

The invention concerns a trocar in the form of a flexible access tube for insertion into body cavities, preferably with the use of an invertible hose system for diagnosis and surgical interventions, particularly in the colon area.

The invention especially concerns a flexible access tube whereby diagnoses can be performed, for example by inserting a coloscope, as well as operations in accordance with the minimally invasive surgery technique, by inserting corresponding surgical instruments into the access tube through the anus. Among other things, this new type of flexible access tube thereby takes over the function of trocars known until now, and for reasons of simplification will be called a "flexible trocar" in the following.

BACKGROUND OF THE INVENTION

When striving towards ever better and more specialized surgical techniques, whereby ever smaller operating areas suffice and are therefore less demanding on the patient's organism, the technically meaningful application of the so-called minimally invasive surgery technique is constantly expanded with the development of new instruments and auxiliary means. Diagnoses as well as complete operations are already being performed on human organs by inserting so-called trocars as auxiliary surgical means through the abdominal wall or the thorax, through which surgical instruments as well as optics can be moved to the organ to be diagnosed or operated.

Such auxiliary means and instruments however cannot be used in all cases.

For example, to surgically remove large tumors such as carcinomas etc. from the colon, except for the end area of the intestine, according to conventional usage required a major operation until now, i.e. the patient's abdomen had to be opened in order to reach the intestine. The basis for this expensive surgical technique, which is extremely demanding on the patient, is among other things that the intestine must be steadied for a precise operation, i.e. the intestine is removed from the respective area of the abdomen and is clamped or steadied by suitable means only then is the surgeon able to remove the tumor by means of precise steps and then close the intestine with sutures.

It is obvious that this intervention not only represents an expensive operation which is very demanding on the patient and could possible entail a great risk, particularly for elderly patients, but that it also incurs great costs which on the one hand are caused by the extensive surgical effort, and on the other by the patient's mandatory long recovery period in the hospital.

Until now it was only possible to remove carcinomas from a maximum depth of about 20 cm from the anus into the intestine without the above mentioned procedure. This takes place by means of a so-called rectoscope. A rectoscope is a rigid cone-shaped tube part which is inserted into the anus and expands the latter by several centimeters. In that way the surgeon has enough space to reach the diseased area of the intestine with special tools and perform the operation.

One disadvantage of this surgical technique however is that the rectoscopy is only suitable for surgical interventions in an area of the colon within the first 20 cm from the anus, and only a few specialized surgeons are able to perform this operation. Starting with this problem it is the task of the invention to create a totally new type of device enabling both diagnoses as well as surgical interventions in the colon area through the end of the intestine.

This task is accomplished by a device with the features of claim 1. Further advantageous configurations of the invention are the subject of the remaining subclaims.

The invention begins with the following consideration: Through endoscopy it is already possible to examine the entire intestine of a patient through the anus by means of so-called coloscopes. These coloscopes are essentially used to visually examine the intestine through the anus. To that effect the distal end of the coloscope is equipped with a lighting device and optics, preferably a camera chip which is connected by lines inside an endoscope or coloscope shaft to a camera control at the end of the shaft. The camera control in turn is connected by a video processor to an external monitor on which the treating physician can see the areas to be examined. The distal end of the shaft being introduced into the cavity is designed to bend in all directions and can be manually curved like a finger by means of a handle, preferably via two steering wheels with a brake in the coloscope's end-section. As a rule at least two channels pass through the coloscope shaft and open at the frontmost point of the distal end. When required, cleaning fluid can be directed through these channels to clean an area to be examined, or $CO_2$ (air) to expand the cavity, or various working tools for example forceps or scissors for removing tissue samples, biopsy needles, heatable cutting wires, coagulation electrodes etc. can be inserted, and can also be manually actuated at the rear end of the coloscope shaft by means of operating wires or Bowden cables inside the internal channel. After the distal end has reached the respective area, a miniature forceps can for example be inserted into the channel from the rear section of the coloscope shaft and be pushed toward the distal end to remove a tissue sample. After the sample has been obtained, the forceps are withdrawn and removed from the channel so that further examination can proceed.

The coloscope generally has a lengthwise extended tubular form with a diameter of about 9 to 15 mm, and consists of a flexible material so that it can follow bends in the cavity to be examined, for example intestinal convolutions.

An endoscope of this type is known from the state of the art, for example according to U.S. Pat. No. 5,259,364, issued Nov. 9, 1993; and U.S. Pat. No. 5,568,968, issued Dec. 24, 1996. This endoscope essentially consists of an endoscope head or distal end to which an endoscope shaft made of a flexible tube body is connected, and an operating device at the rear end of the endoscope shaft. The operating device has a number of actuating wheels which are able to rotate in the endoscope shaft and are actively connected to the distal end by operating wires or Bowden cables located inside the endoscope shaft. A rear end-section of the endoscope furthermore contains a first driving or advancing device which exerts a driving force on the endoscope shaft through driving wheels.

At least the front section of the endoscope shaft has an invertible hose which is driven by a second driving or advancing device. Here the invertible hose consists of an inner hose section which can slide along the endoscope's jacket surface and is inverted to form the front of an outer hose section in the endoscope's distal end area. The front of the outer hose section is furthermore routed back to the second driving device and is attached to its housing. In the endoscope's rear area the inner hose section is inverted to form an external rear hose section, which is also routed to the second driving device and is attached to the axial end of its housing opposite the front of the outer hose section.

Here the second driving device acts on the inner invertible hose section to move it in the axial direction of the endoscope. To that end the second driving device has a kind of sleeve or collar, which contracts in the radial direction and exerts frictional pressure against the inner hose section; it can also move like a piston in the endoscope's axial direction. The radial pressure force of the sleeve is large enough so that at least a portion of the applied pressure force is transmitted through material deformation to the jacket surface of the endoscope shaft, thereby driving the endoscope shaft together with the inner invertible hose.

Since with this only type of driving by the second driving device the advancing speed (and path) of the invertible hose is only half as large in its inverted front area as that of the endoscope shaft, i.e. the shaft would exit from the invertible hose like a telescope with increasing penetration depth, the first driving device mentioned earlier exerts a braking force on the shaft which opposes the advancing force of the second driving device.

In that case the second driving device is synchronized with the first driving device so that, when both devices act together, the axial moving speed of the inner hose section is twice the speed of the endoscope shaft, where the latter slides in relation to the internal shaft (i.e. the distal end of the endoscope shaft moves at the same speed as the turned-up area of the invertible hose).

To facilitate the relative sliding motion between the endoscope shaft and the invertible hose, the state of the art according to further provides a lubricating device, whereby lubricating or sliding means can be forced between the inner hose section and the endoscope shaft as well as between the internal and the outer hose section. To that end the lubricating device has a cone-shaped bushing which slips over the endoscope shaft and acts as a seal with the rear turned-up area of the invertible hose which extends over the cone-shaped bushing. The lubricant, which is forced into the gap between the cone-shaped bushing and the endoscope shaft by a pump, spreads along the entire length between the inner hose section and the endoscope shaft, and excess lubricant flows into the cavity to be examined in the turned-up front area of the invertible hose.

From the in-house state of the art the inventor furthermore knows of an endoscope of this kind which uses a type of double invertible hose system as briefly described in the following:

This invertible hose system has an endoscope shaft that slides in a hose turned up on both sides, which can also be moved by a driving device acting on the inner hose section of the invertible hose. The driving device has at least one continuous advancing means which can be radially pressed onto the inner hose section in order to essentially move the latter continuously in the axial direction of the shaft. This has the great advantage that the continuous advance of the invertible hose system is accurately controllable, for example to precisely locate the distal end of an endoscope.

It is provided in this case that the pressure force exerted by the advancing means on the inner hose section must be such that the shaft makes direct friction contact with the inner hose section, at least in the area of the advancing means. The advancing means is provided by one or several friction wheels which can be preloaded with a predetermined or adjustable pressure force against the inner hose section, so that on the one hand a continuous, and on the other a slip-free advance of the endoscope shaft into a patient's cavity can be assured.

The driving device furthermore has a fixture to synchronize the shaft movement with the invertible hose movement. This can be a rear or front-end fitting or a clamp that is axially affixed to the shaft against which, depending on the advancing direction, the rear or the front turned-up area of the invertible hose abuts and slides, so that the invertible hose can exert a braking force through the rear or the front-end fitting against the force that presently advances the shaft. As an alternative, the synchronization fixture can be a roller or spindle drive acting on the rear end-section of the shaft, which is synchronized with the invertible hose drive so that the advancing speed of the shaft is half the advancing speed of the inner hose section.

The invertible hose can have a guide part or a bushing made of a stiff material which is pulled over the inner hose section and forms an annular gap, where the free ends of outer hose sections are affixed to two axial end-sections of the gap and form two axially separated inverted areas when the inner hose section is turned up and routed back. This bushing now offers the possibility of receiving or attaching a driving device directly to the inner hose section, so that the external size of the entire invertible hose system remains compact and thus improves its maneuverability.

The bushing may further be provided with a number of openings or lengthwise slits in its central section, preferably at the same angular separation from each other. The invertible hose then forms an environmentally sealed empty space over the inner hose section, the outer hose sections as well as the bushing, which only can be accessed through the openings in the bushing. In this way the bushing is constructively prepared to receive a driving device, whose propelling means can contact the inner hose section through the lengthwise slits. Furthermore the bushing is advantageously provided with grooves extending in the axial direction, which open at the front face of the bushing. During operation of the system, these grooves facilitate the forced shifting of the lubricant in the cited cavity through the bushing.

The driving device of the invertible hose system can have a two-part collapsible housing which can be placed around the bushing of the invertible hose in the manner of a sleeve, and in the collapsed state forms an externally sealed empty space with the bushing in which friction wheels are located, which can be pressed against the inner hose section through the openings of the bushing when the housing is collapsed. This achieves a compact, self-enclosed (integrated and not additive) construction of the system increasing the maneuverability and functionality of the interacting parts.

The friction wheels of the internally known endoscope are furthermore placed in springy fashion against the housing, in order to exert a predetermined pressure force that corresponds to the spring force, or which is also adjustable against the inner hose section, and also to allow the use of slightly variable diameters of the shaft. In addition, the running surfaces of the friction wheels can be provided or designed with an anti-slip coating.

The endoscope also has the special technical feature where a connector is installed on the driving device housing for supplying a lubricant which can be pressed into the empty space of the invertible hose through the openings in the bushing. On the one hand this allows to lubricate the drive mechanism itself, and on the other the relative sliding motion of the internal and outer hose sections, thereby reducing the friction.

As a further aspect of the internally known endoscope, the invertible hose system is designed with a lubricating device for pressing lubricant into an annular gap between the shaft and the inner hose section, where at least one radially running hole or perforation is placed in the shaft wall, which opens into the annular gap and is connected to a lubricating device. In this way lubricant can be supplied directly into the annular gap at a low cost.

As an alternative, the lubricating device comprises a rear clamping part, which is affixed to the shaft and has at least one lubricant injection spout. This spout protrudes into the annular gap and enables pressing lubricant through a hollow needle formed inside the spout.

Among other things the lubrication system for supplying lubricant to the invertible hose system has one or two pressure vessels, each able to hold a lubricant bag or bellows designed as a one-way article, which can be fluidly connected by a coupling to supply lines of the shaft and the driving device.

The basic idea of the invention consists in reworking a known endoscope, preferably the one known internally, into an auxiliary surgical means for performing diagnoses and operations in the colon by means of microsurgical techniques, where the endoscope shaft which was described earlier by means of the internal state of the art, is replaced by a flexible access tube produced in accordance with the invention, which in the manner of a trocar makes it possible for surgical tools and diagnostic instruments to access the area to be operated. Experiments have shown that the colon has an elasticity which allows its internal diameter to expand to over 25 mm. Based on these results it is possible to develop a flexible access tube in conjunction with an invertible hose transport system, whose internal diameter allows the insertion of surgical tools and other instruments, such as for example optics or a coloscope shaft into body cavities like the colon e.g.

According to patent claim 1, the access tube of the invention therefore has a flexible outer jacket and a radially separated flexible internal jacket which form a hollow space for supply and function channels between them.

The supply channels are preferably designed as air or $CO_2$ lines and/or as flushing channels, while the function channels contain Bowden cables or hydraulic fluid to actuate the access tube, and camera connection lines for video chips and optical fibers, preferably glass fibers, located at the distal end of the access tube which enable illuminating the cavity to be examined.

The correspondingly large inside diameter of the internal jacket, and the location of the supply and function channels in the space between the external and the internal jackets form a sufficiently large access channel that extends from the anus to any place in the colon at least below the second sigma loop and possibly beyond, but can also be inserted into other body cavities.

With the help of the flexible access tube of the invention it is therefore possible to accurately advance from the anus to the desired area in the colon or beyond it, regardless of the distance from the anus. This creates a quasi surgical channel comparable to a trocar, through which the desired probes and medical tools can be inserted either simultaneously or successively in a simple manner. The risk of injuring the intestinal wall while the surgical tools or examination probes are inserted is thereby eliminated. The operation can proceed faster since no risk of an intestinal wall injury needs to be feared, for example when changing one tool for another, since these procedures only occur inside the trocar, i.e. the instruments are only able to contact the inner wall of the trocar but not the intestinal wall itself.

As mentioned earlier, the trocar interspace, i.e. the space between the internal and external jackets can be used in the most diverse ways. For example two or more air or $CO_2$ channels can be located therein. This allows the intestine to be inflated and thus more uniformly unfolded. In addition two or more suction and/or flushing channels can be provided. This allows the operating field and the integrated optics of the trocar to be flushed, or flushing can take place in predetermined directions. Beyond that several illumination channels can also be formed in order to improve the view and enable to illuminate in predetermined directions.

At its rearmost end-section the trocar of the invention is additionally equipped with a trocar valve and/or a seal. As previously explained, the supply channels are designed to provide $CO_2$ or air, but also flushing liquid. As long as no surgical instrument is inserted into the trocar, the $CO_2$ and/or the flushing liquid escape uncontrolled through the inner trocar space. The trocar valve, preferably in the form of an electromagnetic flap valve, is provided to prevent this by closing the inner trocar space against the outside. This valve opens as soon as a surgical instrument is introduced into the trocar, which causes only minor leaks. These can be additionally minimized with a seal between the trocar and the surgical instrument.

The cited flap valve proved to be particularly suitable with a one-piece or also a two-piece flap with or without a hinge. But inflatable annular packing or hoses around the trocar's internal circumference can be envisioned as valves and simultaneously as seals.

Finally, special function channels can be provided between the external and internal trocar jackets, which are closed at the trocar's distal end and at the rear end are preferably connected to a vacuuming or a pressurizing device. Vacuuming in particular causes the external and internal trocar jackets to press against each other, at least in the area of these function channels, thereby achieving a stiffening or freezing of the flexible trocar's attitude. This is particularly important during the operating phase when the trocar must be kept as rigid and the intestine as unyielding as possible.

Alternatively to the vacuuming process, the special function channels can also be pressurized to achieve a certain temporary rigidity of the trocar. It can also be envisioned to spray a fluid or a gel into the function channels, which hardens and then liquefies under predetermined conditions, e.g. in a temperature-dependent manner.

The invention and its mode of operation will be explained in greater detail in the following by means of preferred configuration examples with reference to the accompanying drawings, wherein:

FIG. 1 is a cross-sectional view of an access tube of the invention (hereafter called a flexible trocar) according to a preferred configuration example of the invention;

FIGS. 2(a) and (b) are cross-sectional views of several alternatives of the construction of flexible trocar according to the invention;

FIG. 4a is an enlargement of the connection area between a discharge hose of a pressurized lubricant container and a supply hose of the trocar-invertible hose system;

FIG. 5a is a lengthwise cut through the rear trocar section enlarged to illustrate the lubricant supply;

FIG. 5b is a cross section of the rear trocar section in FIG. a;

FIG. 6 is an invertible hose construction as used with the trocar-invertible hose system according to the first and second configuration example;

FIG. 6a is cross-sectional view of a drive and guide bushing cut along line A—A in FIG. 6;

Figure 1:
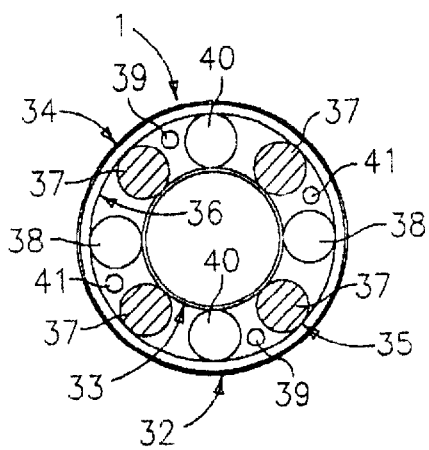

According to FIG. 1, which illustrates a cross section of the trocar according to a first configuration example of the invention, the trocar consists of a highly flexible trocar shaft 1 which is about 70 to 80 cm long or even longer, and is constructed of a flexible external jacket 32 and a flexible internal jacket 33. The internal jacket has a uniform radial distance from the external jacket creating an annular gap between the external and internal jackets.

The external jacket 32 has an outside diameter of about 22 to 25 mm and consists of a leaf spring loosely wound into a helix, preferably made of flat strip steel or a band-shaped plastic, where the distance between two adjacent windings in this external helix is about 2 to 3 mm. The external helix is furthermore covered with a coating or film preferably of Pvc or another plastic, which has a defined abrasion resistance as well as surface roughness, which creates a highly flexible, closed compound material for the external jacket 32. The inside of the external helix could be additionally covered with a thin, preferably plastic coating.

The internal jacket 33 has an inside diameter of about 13–15 mm and consists of a spiral winding, preferably of a round steel wire, which is so tightly wound that in contrast to the external helix, no gaps exist between any two adjacent windings. Because the material selected for the internal spiral winding is round steel wire, it remains highly flexible despite the tight winding.

In this configuration example according to FIG. 1, the external jacket 32 and the internal jacket 33 are coaxially aligned with each other along the entire length, where the radial distance between the external 32 and internal jacket 33 is maintained by axially separated, washer-shaped links or even bushings (not illustrated) along the entire axial length of the flexible trocar 1. The inner and outer radial edges of these links are affixed to the external and internal jackets 32, 33 by clamping and possibly by additional cementing, and thus subdivide the radial or interspace gap into several chambers. In addition the individual links are penetrated by a number of holes at a uniform angular distance from each other and interconnect the chambers, thus enabling the insertion of channels or hoses which will be individually explained in the following (for light, water, hydraulics, electricity, etc.).

The space or the annular gap between the external and internal jackets is used as follows: At least two, but according to this configuration example four function channels are placed at equal angular distances from each other through four holes in the individual links, into which four Bowden cables 37 are inserted. One end of these Bowden cables 37 is attached to a distal end-section 3 of the trocar shaft 1, and their respective opposite end is articulated with handles 4, preferably hand wheels so that, as is customary for example with endoscopes, the highly flexible distal end of the trocar shaft 1 can be bent in every desired direction. This accomplishes that every bend of the intestine can be followed and the distal end can be located anywhere on the intestinal wall.

Two diametrically opposed air or $CO_2$ channels 39 are arranged symmetrical with equal distances between them. The same applies to two flushing and/or suction channels 40 and two optical lines for one camera chip each, which are located at the distal end of the trocar 1 and are connected by lines to a videoprocessor. The arrangement of two camera chips offers excellent fail-safety, since even if one camera fails the other permits continuing the operation. Beyond that two optical fiber lines 41 are provided for connection to a cold light source to illuminate the operating area.

The air or $CO_2$ channels, the flushing/suction channels and the channels for the light conductors (glass fiber lines) and the optical lines represent the supply channels of the system. As an alternative to the above mentioned Bowden cables, hydraulic or pneumatic lines can of course be envisioned as function channels for actuation, i.e. movement of the trocar.

Figure 2A:
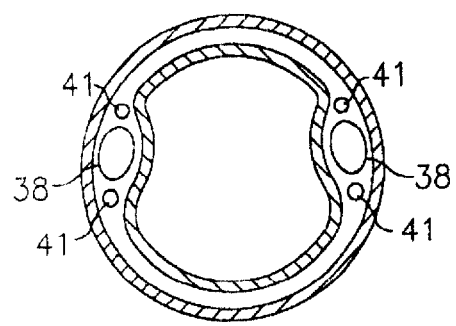
FIG. 2c is a fragmented side elevational view of the inner and outer tubular components of the flexible trocar showing a preferred spiral construction of these elements.

FIGS. 2(a) and (b) illustrate alternatives of a cross-sectional construction of the trocar, which are also possible.

In FIG. 2(a) the gap between the external jacket 32 and internal jacket 33 is designed wider on the left and the right side, providing sufficient space to symmetrically arrange one each camera line 38 and two each illumination lines 41. This allows the gap in the other areas to be smaller, so that more space is available in the internal jacket 33 to introduce one or several instruments.

The trocar consists of a highly flexible trocar assembly 1 which is about 70 to 80 cm long or even longer, and is constructed of a flexible external jacket 32 and a flexible internal jacket 33. The internal jacket has a uniform radial distance from the external jacket creating an annular gap between the external and internal jackets. The external jacket 32 has an outside diameter of about 22 to 25 mm and, as noted in FIG. 2(c), consists of a leaf spring loosely wound into a helix, preferably made of flat strip steel or a band-shaped plastic, where the distance between adjacent windings 32a and 32b is about 2 to 3 mm. The external helix is preferably covered with a coating or film 32c, preferably of PVC or another plastic, which has a defined abrasion resistance as well as a surface roughness, which creates a highly flexible, closed compound material for the external jacket 32. The inside of the external helix could be additionally covered with a thin, preferably plastic coating.

Figure 2B:
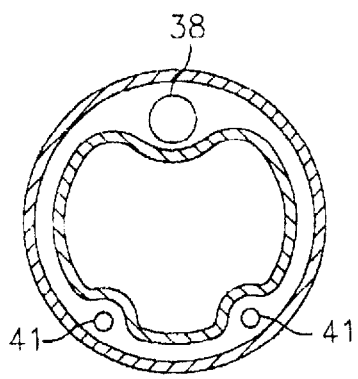
Figure 2C:
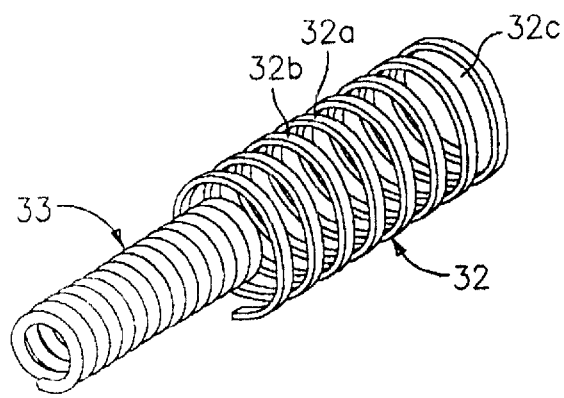

The internal jacket 33 has an inside diameter of about 13–15 mm and, as shown in FIG. 2(c), consists of a spiral winding, preferably of a round steel wire, which is tightly wound that in contrast to the external helix, so that no gaps exist between any two adjacent windings. Because the material selected for the internal spiral winding is round steel wire, it remains highly flexible despite the tight winding. In this configuration example, the external jacket 32 and the internal jacket 33 are coaxially aligned with each other along the entire length, where the radial distance between the external 32 and internal jacket 33 is maintained by axially separated, washer-shaped links or even bushings (not illustrated) along the entire axial length of the flexible trocar 1. The inner and outer radial edges of these links are affixed to the external and internal jackets 32, 33 by clamping and possibly by additional cementing, and thus subdivide the radial or interspace gap into several chambers.

In FIG. 2(*b*) the gap between the external 32 and internal jacket 33 is radially enlarged in at least three, preferably four areas located at equal angular distances from each other. A camera line 38 is provided in the upper radial expansion of FIG. 2(*b*). Two illumination lines in the form of optical fiber cables 41 are provided in the two lower radial expansions in FIG. 2(*b*). I.e. only the minimally necessary function and/or supply channels are provided, so that the open cross section inside internal jacket 33 can be as large as possible.

As illustrated in FIGS. 2(*a*) and 2(*b*), the respective radial expansions form rib-shaped protrusions extending at least radially inward, which preferably extend throughout the entire trocar and support the sliding surgical instrument or an endoscope shaft to be inserted. This essentially reduces the frictional resistance between the surgical instrument and the trocar. Additional protrusions can of course be provided, independently of the above described expansions in the trocar's internal jacket.

To further reduce the friction it is also advantageous to line the inside of the trocar with a layer of teflon or a comparable material, at least in the area of the inward extending protrusions.

It can be envisioned in all cases to immediately provide several internal jackets to form several access tubes, so that several instruments or probes each have their own access tube. However, depending on the diameter of the individual instruments, several of them can be inserted simultaneously next to each other in a single access tube.

Depending on the individual application instance, all imaginable variations of the internal space configuration are possible. However it was shown that the symmetrical arrangement of the function and/or supply channels in the annular gap between the external and internal jackets 32, 33 of the trocar 1 of the invention is preferable to an asymmetrical arrangement, since it achieves a homogeneous bending of the trocar 1, perhaps when the Bowden cables are actuated. This also means that the actuation forces in all the Bowden cables are the same for bending the distal end 3 of the trocar 1 in any direction, thus improving the ability to position and handling the trocar 1. Insofar as an asymmetric arrangement may be required for especially large instruments being guided through the internal jacket 33, a distribution of the supply and function channels must be provided as a function of their flexural strength properties, so that here as well the result is as homogeneous as possible a bending characteristic throughout the entire circumference of the trocar 1.

Figure 4:
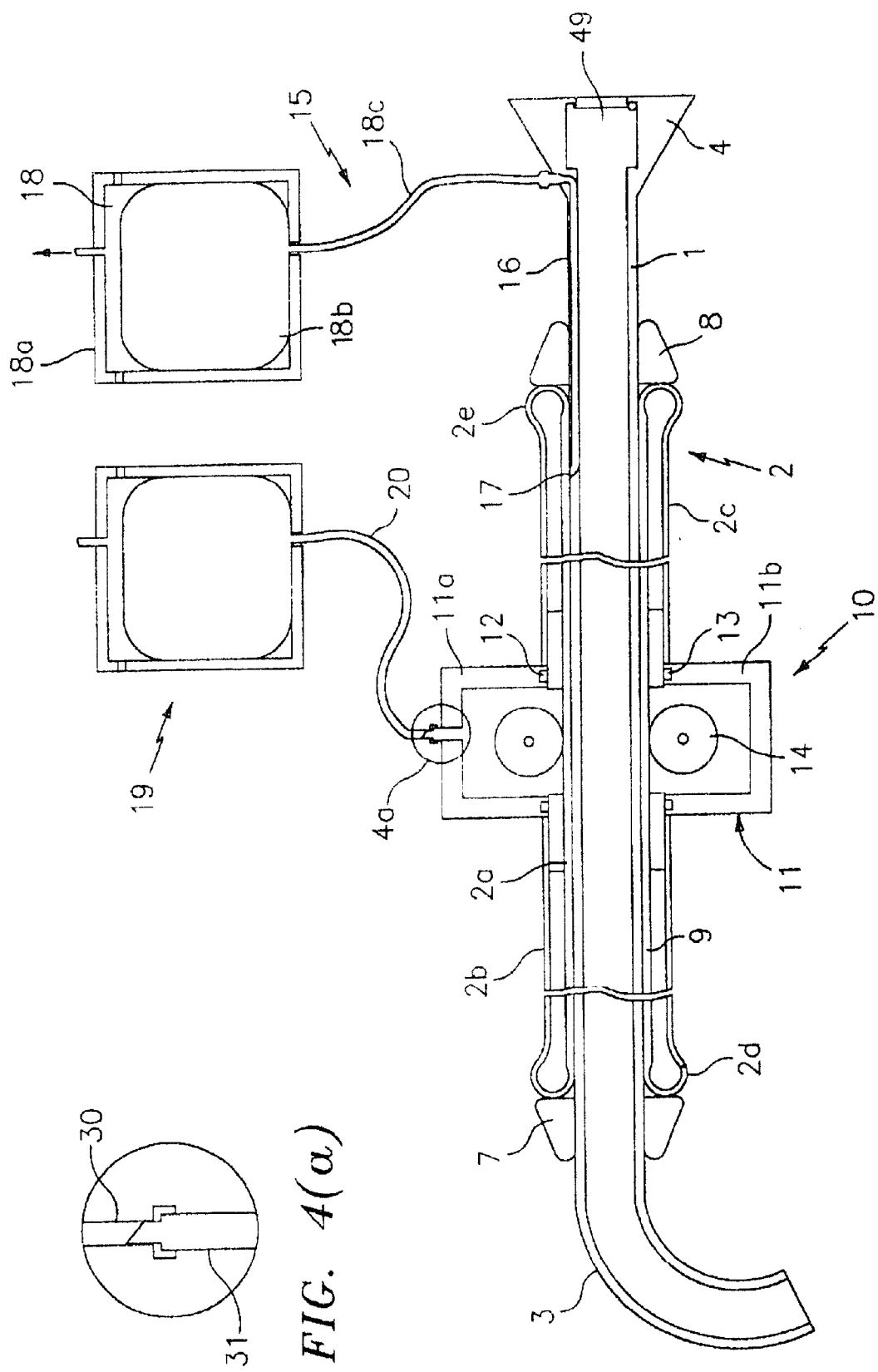
FIG. 4 is the trocar-invertible hose system with the integrated trocar lubrication and friction drive according to the first configuration example of the invention.

FIG. 4 represents the schematic side view of a trocar-invertible hose system according to a first configuration example. According to FIG. 4 the trocar-invertible hose system consists of a trocar, i.e. the trocar shaft 1 whose construction was explained earlier, which is encased along a length of about 75 to 100 cm by an invertible hose 2 of the dual inversion type, or which is invertible on both sides. So that the distal end piece 3 of the trocar shaft 1 can be actuated by the Bowden cables referenced in FIG. 1 by 37, it is functionally connected to a manual actuation device 4 located inside a housing in a rear end-section of the trocar shaft 1.

As can be seen in FIGS. 4 and 6 in particular, the invertible hose 2 of the invention consists of an inner hose section 2*a* which slides through a driving and guiding bushing or a hose guiding part 5, and its front (inverted) area is turned up into the front of an outer hose section 2*b*. Here the front of the outer hose section 2*b* is returned to the driving and guiding bushing (hose guiding part) 5, which consists of a stiff preferably a plastic material, and one axial end is attached to the driving bushing 5 so that it is positioned between the internal 2*a* and outer hose section 2*b*.

In a rear (inverted) area, the inner hose section 2*a* is turned up into an external rear hose section 2*c*, which is returned to the driving bushing 5 and is affixed to an axial end of the driving bushing 5. On the one hand the driving bushing 5 is used as the guide element for the inner hose section 2*a*, to prevent buckling and wrinkling as well as scale formation, and on the other hand as a connecting part of the external front 2*b* and the external rear hose section 2*c*, where a central area of the driving bushing 5 remains exposed, i.e. not covered by the inverted hose 2. The driving bushing 5 has at least one opening in this central section, preferably a lengthwise slit 6 of a predetermined width extending axially. Presently four lengthwise slits 6 are provided at equal angular distances from each other, as shown in particular in FIG. 6*a*. The driving bushing 5 in FIG. 6*a* furthermore has a number of continuous lengthwise grooves 5*a* on its inside, which open to the front of the driving bushing 5. Here the lengthwise grooves 5*a* may be drawn parallel to the axis or spirally.

As can be seen particularly in FIG. 4, the material i.e. the type of material and the thickness of the invertible hose 2 are designed so that a bead-shaped expansion forms in each front and rear inverted areas 2*d*, 2*e* due to the material bunching at the inversion, which internally leads to a predetermined narrowing of the inside diameter of invertible hose 2.

According to FIG. 4, the front area 2*d* of the invertible hose 2 slides against a cone-shaped front clamping part 7, which is secured to the trocar shaft 1 at least in the axial direction and tapers conically in the penetration direction of the trocar shaft 1. The inverted rear area 2*e* of the invertible hose 2 also slides against a rear clamping part 8, which in this special configuration example is also secured to the trocar shaft 1 and also has a corresponding shape. The rear clamping part 8 however tapers conically in the opposite direction to the trocar's penetration. It should however be pointed out here that at least the rear clamping part 8 can have any external shape since it is not inserted into the cavity to be examined.

FIG. 4 furthermore shows clearly that a small annular gap 9 is formed between the inner hose section 2*a* of the invertible hose 2 and the trocar shaft 1, which is axially limited by the two beads in inverted areas 2*d*, 2*e* of the invertible hose 2, and forms a seal against the outer jacket surface, i.e. the external jacket of the trocar 1.

A driving or advancing device 10 is placed around the central area of the driving bushing 5. Here the advancing device 10 consists of a housing 11 preferably made of plastic or a rustproof metal alloy, wherein the drive mechanism for the invertible hose 2 according to the first, second and third configuration example of the invention is located, and is further described in the following. The housing 11 itself consists of two cup-shaped housing halves 11*a*, 11*b*, which can be opened at a free edge section along the driving bushing 5 by means of a not illustrated joint or hinge, and can be locked in the opposite free edge section by means of an also not illustrated bolting device. As an alternative, the housing halves 11*a*, 11*b* can also be completely separated and joined by means of two bolting devices. The lateral walls of the housing 11 extending crosswise to the driving bushing 5 have recesses at each housing half 11*a*, 11*b* which are adapted to the external cross-sectional shape of the driving bushing 5 and, when the housing 11 is collapsed and bolted, form a self-enclosed recess or open profile which corresponds to the contour of the driving bushing 5 and tightly seals the latter against the outside. The recesses and the free edges of the housing halves 11a, 11b are equipped with grooves 12 (not illustrated) at their respective cut or edge surfaces, into which sealing strips 13 are clamped or cemented and apply tightly against the jacket surface of the driving bushing 5 when the housing halves 11a, 11b are collapsed, in order to tightly seal the inner space of the housing.

The cross section of the present driving and hose guiding bushing 5 has a circular contour which corresponds to the circular cross section of the invertible hose 2, to ensure as tight and tension-free a connection with the inverting hose as possible. However, it may also have a lens-shaped or other cross-sectional form depending on the design of the drive mechanism.

According to the preferred first configuration example, this drive mechanism comprises a not further illustrated drive motor, which acts on a number of friction wheels 14 via a gear cable (not illustrated either). These friction wheels 14 are located on both housing halves 11a, 11b so that in the collapsed or closed condition of the housing 11 they penetrate into a lengthwise slit 6 of the driving bushing 5, and exert friction against the inner hose section 2a of the invertible hose 2 at a predetermined pressure which can preferably be adjusted with springs. The running surface of each driving wheel 14 is preferably coated with an adhesive layer (containing ceramic particles or metal granules of a predetermined grain size) to increase the coefficient of friction between the invertible hose 2 and the driving wheel 14. Alternatively the friction wheels 14 can also be entirely manufactured of a corresponding material, for example an abrasive ceramic. The pressure force is furthermore chosen as a function of the material and the wall thickness of the invertible hose 2, to ensure a uniform, essentially non-slipping advance of the invertible hose 2 through the friction wheels 14.

The trocar-invertible hose system according to the preferred first configuration example of the invention is furthermore equipped with a lubrication system to lubricate the relative sliding motion between the trocar 1 and the inner hose section 2a, and between the internal and outer hose section 2a, 2b, 2c, which is described in the following.

This lubrication system comprises a first lubricant conveying and supplying device 15 with a compressed air pump (not illustrated) or a compressed air connector which is attached to a pressurized container 18 in order to pressurize it or supply compressed air to it. This pressurized container 18 has a cover 18a which can be opened or removed, whereby a loading and unloading opening can be closed. Inside the pressurized container 18 is a removable or exchangeable plastic or rubber bag 18b, or alternatively a lubricant bellows which is filled with the lubricant to be used. This bag or bellows 18b has a discharge hose 18c which passes through a hole in the pressurized container 18 preferably located opposite the pump connection. The hole seals the discharge hose 18c and for that purpose a packing strip is placed in the hole in this configuration example. In addition or alternatively to this seal, the bag 18 fits tightly against the pressurized container wall, so that the discharge hole is essentially airtight and is separated by the bag 18b from the pump connector which is preferably located in the cover 18a.

The free end of the discharge hose 18c has a coupling part 30, which can be connected with a corresponding counterpart coupling part 31 on a supply hose 16 of the trocar-invertible hose system, which protrudes laterally from the rear end-section of the trocar shaft 1, especially from the housing of the actuation device 4. As indicated in FIG. 4, the supply hose or channel 16 is placed inside the trocar shaft 1, i.e. in the annular gap between the external jacket 32 and the internal jacket 33 of the trocar 1, up to a discharge hole 17 in the external jacket 32 of the trocar shaft 1 in the area of the invertible hose 2.

FIG. 4 schematically illustrates the two coupling parts of the discharge 18c and the supply hose 16.

Accordingly the coupling part 30 has a coupling flange with a sleeve nut or a bayonet fastener, and the end of the discharge hose 18c is closed by a diaphragm. The other coupling part 31 has an counterpart that corresponds to the sleeve nut or the bayonet fastener, and the far end of the supply hose 16 is a hollow needle or one equipped with a blade. When the two coupling parts 30, 31 are connected, the hollow needle penetrates through the diaphragm and thereby provides a fluid connection between the discharge hose 18c and the supply hose 16.

It should be pointed out that the coupling 30, 31 must not necessarily be located on the trocar 1. For example the coupling part 30 can also be integrated into the hole of the pressurized container 18, where in that case the counterpart 31 can be directly placed on the bag 18b, thus automatically establishing a connection to the trocar 1 when the bag 18b is used. In that way the first configuration variation is to be preferred since, when the two hoses 18c and 16 are connected, the entire length of the discharge hose 18c is already filled with lubricant and subsequent venting of the lubrication system is no longer required.

As further shown in FIG. 4, the supply hose 16 passes through the discharge hole or holes 17, in a way so that no lubricant can leak into the trocar gap and thus into the access channel of the internal jacket; it ends here in the annular gap 9 between the inner invertible hose section 2a and the trocar shaft 1, which is axially limited and rendered fluid-proof by the front and rear inverted area 2d, 2e. Instead of the at least one discharge hole 17, the external jacket 32 of the trocar shaft 1 can of course be provided with a perforation in the corresponding place, where the annular gap of the trocar shaft 1 can have its own lubricant line 16 with several discharges to the jacket surface, preferably between the windings of the external helix.

Furthermore according to FIG. 4, the rear end-section of the trocar has a magnetic or electromagnetic flap valve 4a which closes the inner space of the trocar to the outside. This valve essentially consists of one or two flaps, which are linked to the trocar by a hinge and can be actuated by means of an electromagnet. This completely prevents any leakage from the distal end through the inner space to the trocar's end-section.

The pressure of the first lubricant conveying device 15 is furthermore designed so that the resulting dynamic pressure inside the annular gap 9 between the trocar shaft 1 and the inner hose section 2a is smaller than the pressure of the bead-shaped inverted areas 2d, 2e of the invertible hose 2 on the trocar shaft 1. In that case the inverted areas 2d, 2e together with the shaft 1 work directly as seals which prevent any lubricant leaks. This has the further advantage that at the moment this type of seal need not slide along the trocar shaft 1 or along the front end part 7 under the respective pressure, but according to the system rolls over the trocar shaft 1, which does not require increasing the necessary advancing force on the inner hose section 2a to overcome friction forces. In turn this leads to a diminished pressure force of the friction wheels 14 on the inner hose section 2a. This also ensures that the trocar shaft 1 can rotate inside the invertible hose 2, thereby enabling passage through the intestine in the presence of abnormal intestinal convolutions.

The lubrication system furthermore comprises a second lubricant conveyance and supply device 19, which is connected by a supply hose or channel 20 to the housing 11 of the driving device 10. The construction of the second lubricant conveyance and supply device 19 corresponds in principle to that of the first lubricant conveyance and supply device 15 or its described alternatives, so that reference to the corresponding text areas can be made here.

By contrast and as already indicated, the second lubricant conveyance and supply device 19 is connected to the drive housing 11 to press the conveyed lubricant into the tightly sealed inner space of the drive housing 11, where the coupling is located directly on the housing 11. Through the openings or lengthwise slits 6 in the driving bushing 5, this lubricant furthermore reaches the hollow space between the internal and outer hose section 2a, 2b, 2c of invertible hose 2, to lubricate the relative sliding motion between the internal and outer hose section 2a, 2b, 2c. Beyond that and inside the drive housing 11, the lubricant of course also provides lubrication to the drive mechanism, i.e. the friction wheel 14 bearings themselves.

Figure 3:
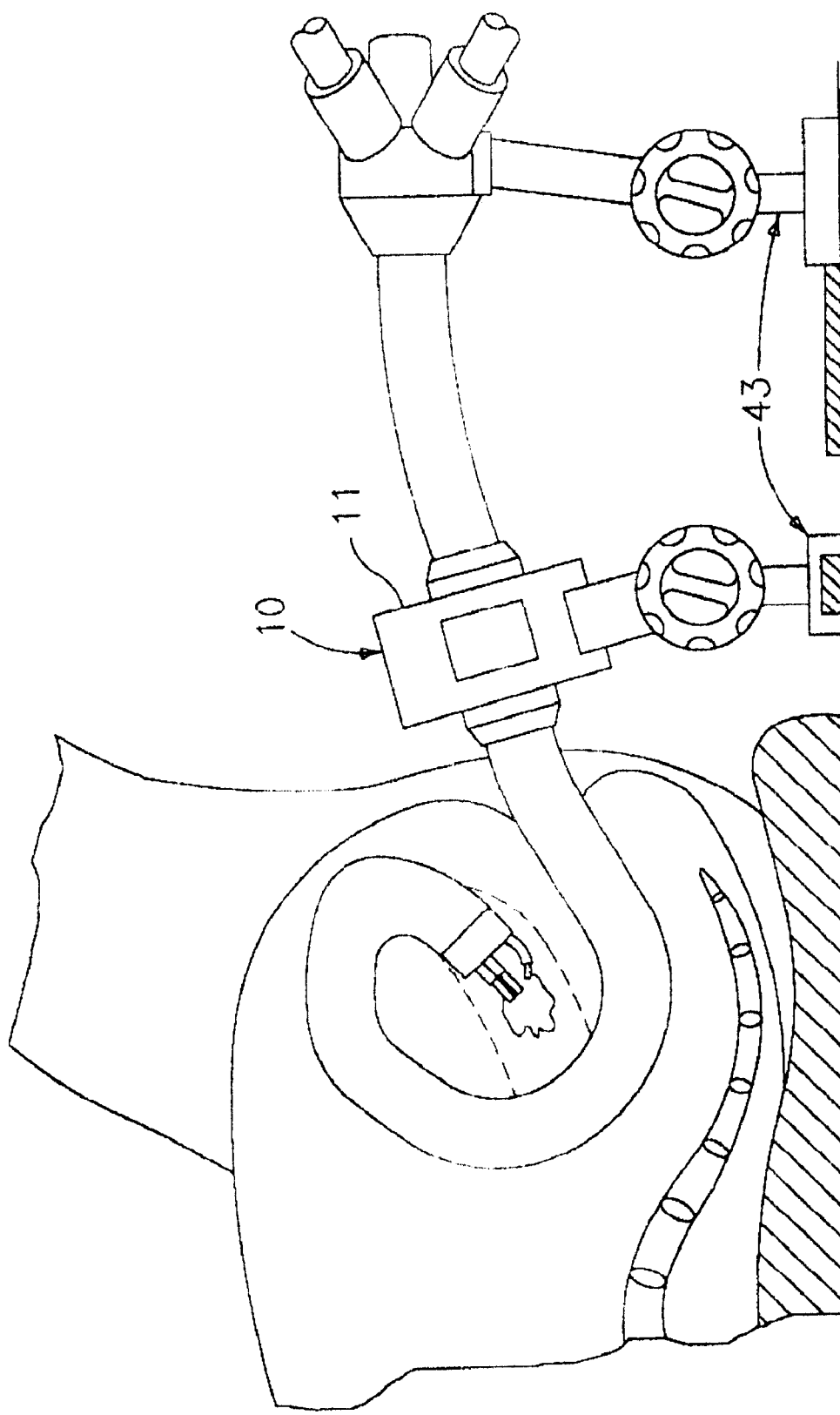
FIG. 3 is a side view of the total arrangement of the flexible trocar of the invention in its working position, and its invertible hose transport system.

The following applies to the function and operation of the trocar-invertible hose system according to the first configuration example of the invention:

As illustrated in FIG. 3, in order to insert the trocar 1 or the trocar shaft into a patient's intestine through the anus, the drive mechanism 10, i.e. the drive housing 11 is mounted on a pedestal 43 with adjustable height, which swivels in every direction with respect to a bed 42 on which the patient lies at least partially, so that the distal end 3 of the trocar shaft 1 can be adapted to the patient's individual body shape. The distal end 3 of the trocar shaft 1 is then inserted for a short distance into the anus until the invertible hose 2 passes the sphincter. It proved to be particularly advantageous to round off the trocar point, i.e. the front edge on the distal end of the trocar shaft, to prevent injuries to the intestinal wall.

$CO_2$ gas is then introduced through the trocar shaft 1 or its internal supply channel into the intestine in order to expand it, whereupon the driving device 10 is actuated to drive the friction wheels 14 (not illustrated) at a predeterminable rpm rate which can also be changed during operation. At this rpm rate the inner hose section 2a slowly advances in the insertion direction of the trocar 1, thereby continuously inverting the hose in the front inversion area 2d into the front of outer hose section 2b, laterally lining the intestinal wall. The driving force of the friction wheels 14 is simultaneously also transmitted to the trocar shaft 1, since the driving force of the friction wheels 14 on the relatively soft inner invertible hose section 2a presses the latter onto the trocar shaft 1, and carries it along through the friction forces, despite the expanding lubricant. I.e. due to the advance of the inner hose section 2a, the trocar shaft 1 is carried along through the friction force between the invertible hose 2 and the shaft 1, perhaps also slightly through the pressure force in the advance direction between the front the inverted area 2d and the front clamping part 7 of the trocar shaft 1, thus inserting it into the intestine.

In order not to allow the advance speed of the trocar shaft 1 to increase beyond the insertion speed of the invertible hose 2, as already explained in detail it is necessary to hold back or brake the trocar shaft 2 (sic) with respect to the inner hose section 2a. According to FIGS. 4–8 this occurs presently through the rear clamping part 8, against which the rear inverted area 2e of the invertible hose 2 abuts, which is forced to move at the same speed as the front inverted area 2d and thereby synchronizes the advance speed of the trocar shaft 1 in relation to the insertion speed of the invertible hose 2 (i.e. the rear clamping part 8, which is secured to the trocar shaft 1, holds it back and thereby guides the reactive force into the rear of the invertible hose section 2c). Accordingly the insertion speed of invertible hose 2 is the same as that of the trocar shaft 1.

It should be pointed out here that during the synchronization process of the advance movements of invertible hose 2 and the trocar shaft 1, the latter slides over the front and rear beads and the area of the driving bushing 5 at the inner invertible hose section 2a, where the sliding speed of the trocar shaft 1 in relation to the forward and rear bead, i.e. in the inverted areas 2d and 2e or in relation to the inner hose section 2a, is however only half the absolute speed of the inner invertible hose section 2a.

In order not to allow the braking forces on the rear inverted area 2e to become too large, and possibly prevent an upset of the invertible hose 2 in the rear of the outer hose section 2c through the braking forces being applied, it is necessary to keep the friction forces between the trocar shaft 1 and the inner hose section 2a small.

As already described earlier, an almost continuous lubrication film is formed in the annular gap 9 between the trocar shaft 1 and the inner hose section 2a and also in the area of the driving device 10, which barely enables an advance of the trocar shaft 1 essentially through the friction wheels 14, but also reduces the friction created by the mentioned relative movement between the two components. Beyond that the inverted areas 2d, 2e and the front and rear clamping parts 7, 8 do not require heavy pressure against each other, due to the small advance force on the forward clamping part 7 or the required small braking force on the rear clamping part 8, for example to obtain a sealing effect as was heretofore the case in the state of the art, since this sealing effect is already obtained by the interaction between the bead-shaped inverted areas 2d, 2e and the trocar shaft 1. Incidentally, the second lubricant conveying device 19 presses the lubricant into the hollow space between the internal and outer hose section 2a, 2b, 2c at a predetermined pressure, thereby further reducing the friction forces. starting a small leak could suffice here to fill the hollow space between the external and internal hose section, i.e. it may not be necessary to inject lubricant during a treatment.

The interaction of the friction wheels 14 as a continuous joint drive for the invertible hose 2 and the trocar shaft 1, that of the forward and rear bead as seals together with the trocar shaft 1, and the continuous lubricant film between the inner hose section 2a and the shaft 1 allow to perform an extremely accurate and precise controllable advance of the trocar shaft 1.

It should be pointed out here that instead of the rear clamping part 8 an additional external synchronization-driving device can be provided, which acts on the trocar shaft 1 through a number of friction wheels and thus ensures the continuous insertion movement of the trocar. Furthermore instead of the friction wheel construction, a spindle drive can be provided as an external synchronization-driving device for the continuous controlled advance of the trocar shaft 1.

In order to precisely place the distal end of the trocar 1, the Bowden cables 37 are actuated accordingly with the servicing part 4, which at least causes the distal end piece 3 to bend in the desired direction. The camera chips and the cold light source with the pertinent optical fiber cables are used here as the monitor and visual examination instrument for the future operation area.

It is apparent that the flexible trocar 1 must be held as immobile as possible for an accurate operation. One fastening possibility consists in using another conventional trocar, which in case of an intestinal operation is introduced through the patient's abdomen, then insert a fastening instrument to the outside of the intestine and clamp the flexible trocar 1 through the intestinal wall. Another possibility is to stiffen the flexible trocar 1, preferably under x-rays or ultrasound control. For example the Bowden cables 37 could simultaneously be shortened, causing the trocar 1 to contract due to the looser winding of the external helix, until the windings of the external helix are close to each other, which compresses the external jacket 32 into a rigid tube. stiffeners or rods can also be inserted into open function channels to provide bending stiffness to the external jacket of the trocar 1.

After the trocar 1 has been fastened inside the intestine, a surgical instrument can be inserted to the operation area through the internal jacket 33, and the operation can begin under continuous monitoring via the camera chip and/or the optics.

To that end the outline of the tumor to be removed can be marked in the intestinal wall with a number of holes made by a laser for example, or simply with knife cuts, where these holes can be seen with light from cold light lines shining through another trocar which is inserted through the abdomen. In this way the external trocar can remove the tumor without taking the intestine out of the abdominal cavity. An operation is of course also possible exclusively from the inside, i.e. by means of the flexible trocar 1.

The withdrawal of the trocar 1 at the end of the operation essentially takes place in the same manner as the insertion process, in this case however the front clamping part 7 takes over the synchronization of the moving speeds between the trocar shaft 1 and the invertible hose 2, while the rear clamping part 8 remains mostly unused.

A second preferred configuration example of the invention is described in the following using FIGS. 5, 5*a* and 5*b*, and only the features which differ from the first configuration example will be mentioned.

Figure 5:
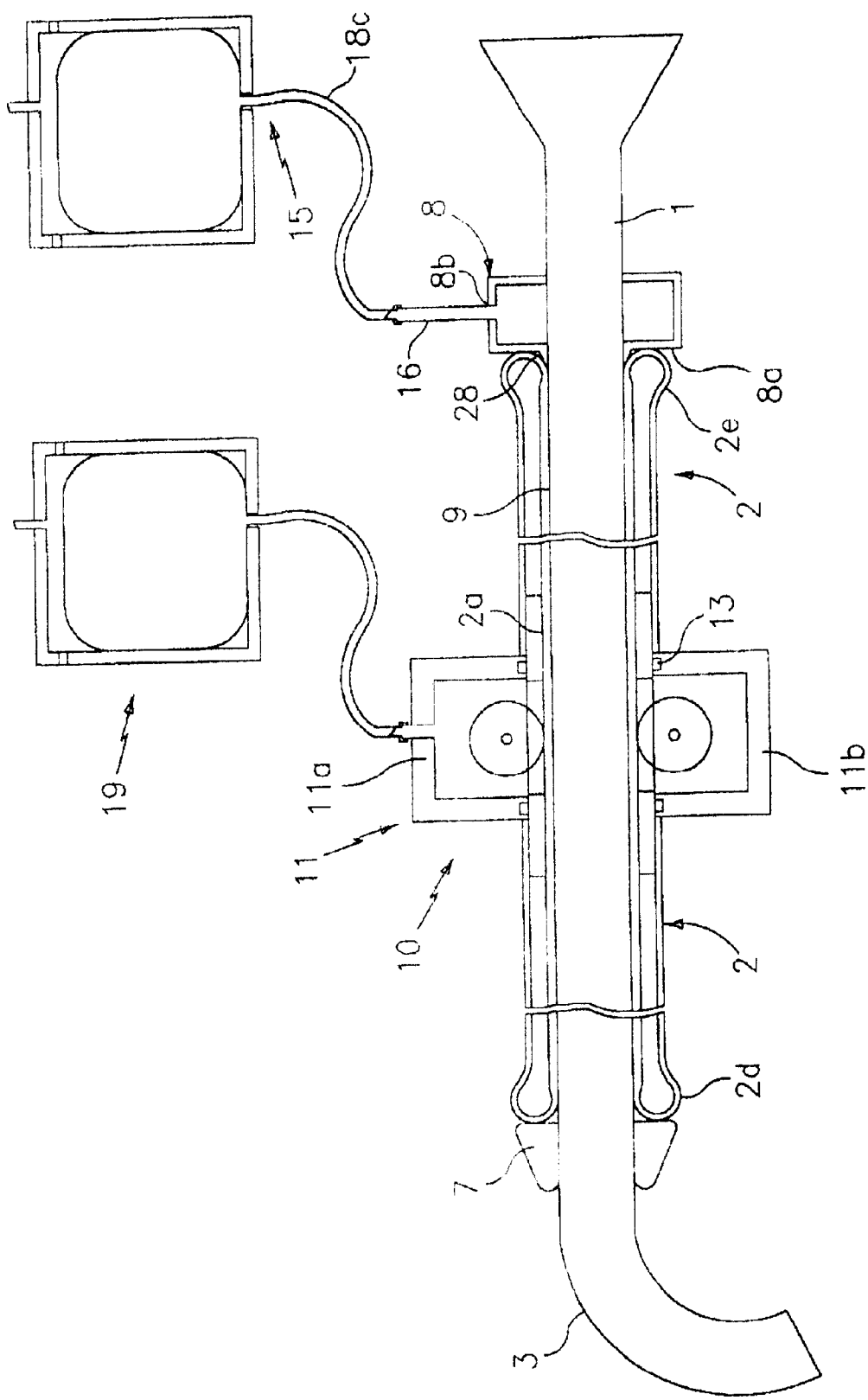
FIG. 5 is the flexible trocar-invertible hose system with trocar lubrication rear clamping part according to a second configuration example of the invention, where the latter is connected to a lubricant injection spout.
Figure 5C:
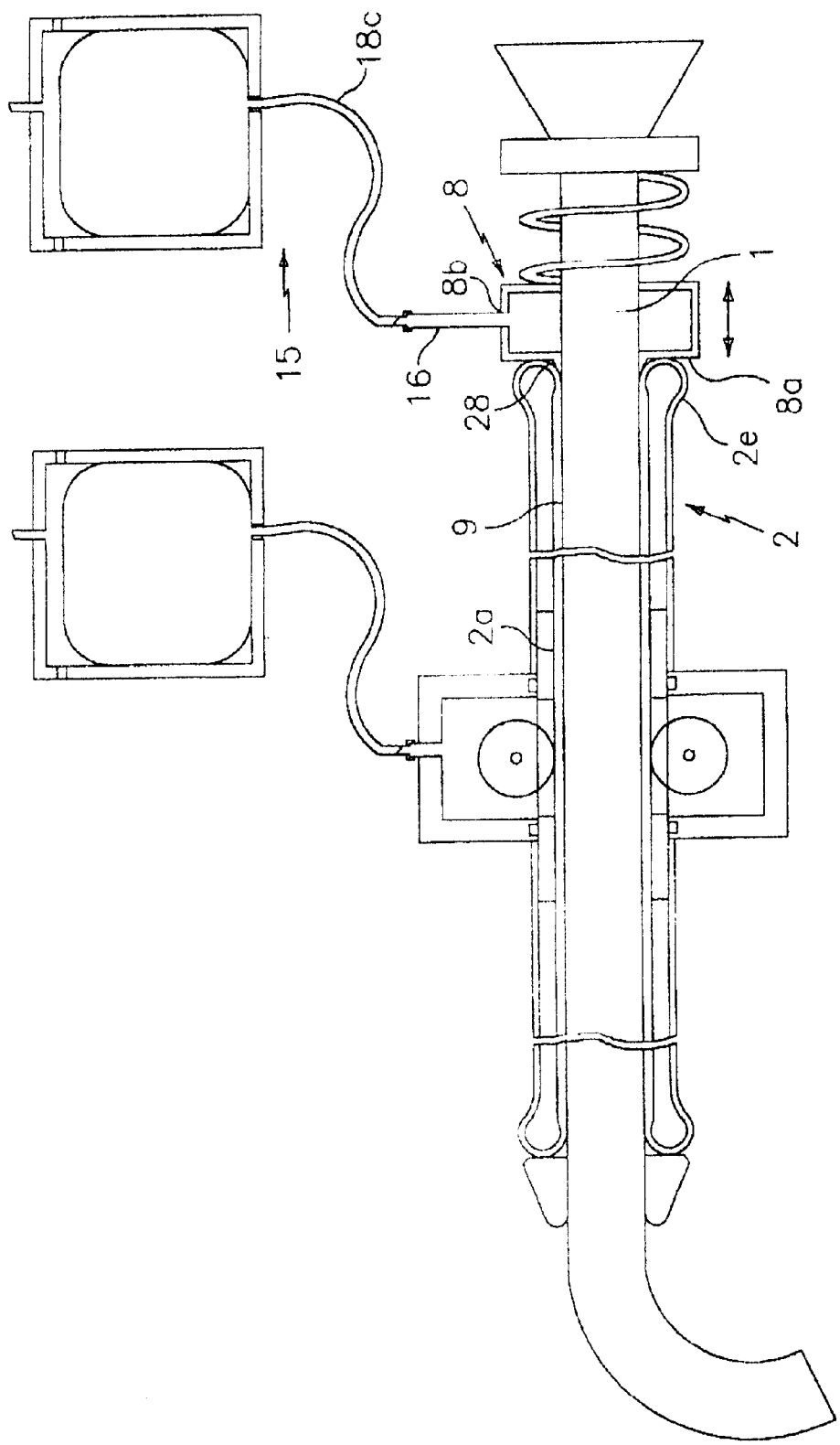
FIG. 5c is a variation of the configuration example in FIG. 5, where the rear clamping part has a sliding part which is pressed by a spring against the invertible hose to ensure that no gap (slippage) occurs between the clamping parts and the invertible hose during the trocar movement (insertion/removal).

As shown in FIG. 5, the rear clamping part 8 of the second configuration example of the invention is designed as a hollow sleeve, which together with the trocar shaft 1 forms an essentially closed hollow space. The rear hollow sleeve can preferably be separated into two symmetrical half shells for better positioning against the trocar shaft 1. The application side or wall 8*a* of the sleeve-shaped clamping part 8 facing the invertible hose 2 has at least one lubricant injection spout 28 in the trocar shaft 1 area, which protrudes toward the invertible hose 2. A cross section of this spout 28 is particularly shown in FIG. 5*b*. Accordingly the lubricant injection spout 28 forms at least ⅓ or ½ of a circle around the trocar shaft 1. Preferably two diametrically adjacent lubricant injection spouts 28 are provided, although FIG. 5*b* only shows one spout. According to FIG. 5*a*, for simplicity's sake the above described hollow space can also be replaced by a channel for supplying the lubricant. Furthermore at least the outermost end-sections of the lubricant injection spouts 28 are flexibly placed on the external jacket surface of the trocar shaft 1, and each has at least one lubricant channel as shown in FIG. 5*a*, which at the rear end (root) of the lubricant injection spout 28 opens into the hollow space or the supply channel of the sleeve, and at its free forward end into the annular gap 9.

As an alternative to the above described lubricant injection spout 28, a number of mere cutouts or notches (not shown in detail) can be provided in the lateral wall 8*a* of the sleeve 8, forming a discharge clearance or gap between the trocar shaft 1 and the application wall 8*a*.

The clamping part 8 is furthermore equipped with a line connector 8*b* which has a fluid connection to the first lubricant conveying device 15 via the supply line 16 and the discharge hose 18*c*. All other parts of the trocar-invertible hose system in FIG. 5 correspond to those of the first configuration example.

During operation of the trocar-invertible hose system according to the second preferred configuration example of the invention, the first lubricant conveying device 15 supplies lubricant to the hollow space inside the rear sleeve-shaped clamping part 8, which is thereby filled. At a predetermined pressure inside the hollow space, the lubricant flows from the lubricant channel into the lubricant injection spout 28, or from the gaps in the application wall 8*a*, and penetrates into the annular gap 9 between the trocar shaft 1 and the inner hose section 2*a* of the invertible hose 2 to lubricate the relative sliding motion of both components. To prevent leaks from the lubricant injection spout 28 or the discharge gap of the rear clamping part 8, the rear inverted area 2*e* of the invertible hose 2 acts as a seal against the trocar shaft 1 and the application side 8*a* of the rear clamping part 8. The rear area of the invertible hose also encloses and seals the lubricant injection spout 28 along its full length.

This measure makes the expensive installation of additional lubricant channels in the space between the external 32 and the internal jacket 33 of the trocar 1 unnecessary, which further increases the open cross section through which surgical instruments are inserted.

It should finally be pointed out with respect to the first and the second configuration example that the trocar 1 drive in particular can be achieved with components that differ from the friction wheels 14. Thus gear wheels can be provided for example for the conveying device 10 of the invertible hose 2, which act on the inner hose section 2*a*. However all of these variations have in common that the pressure force in the radial direction is sufficient to press the inner hose section 2*a* against the trocar shaft 1 for its continuous drive despite the presence of lubricant, which makes it possible to position the distal end 3 precisely in an area to be examined and operated.

A third preferred configuration example will finally be explained in greater detail in the following with reference to FIG. 7, where only the components that differ from the previous configuration examples will be addressed. All other features correspond to the first or the second configuration example.

Figure 7:
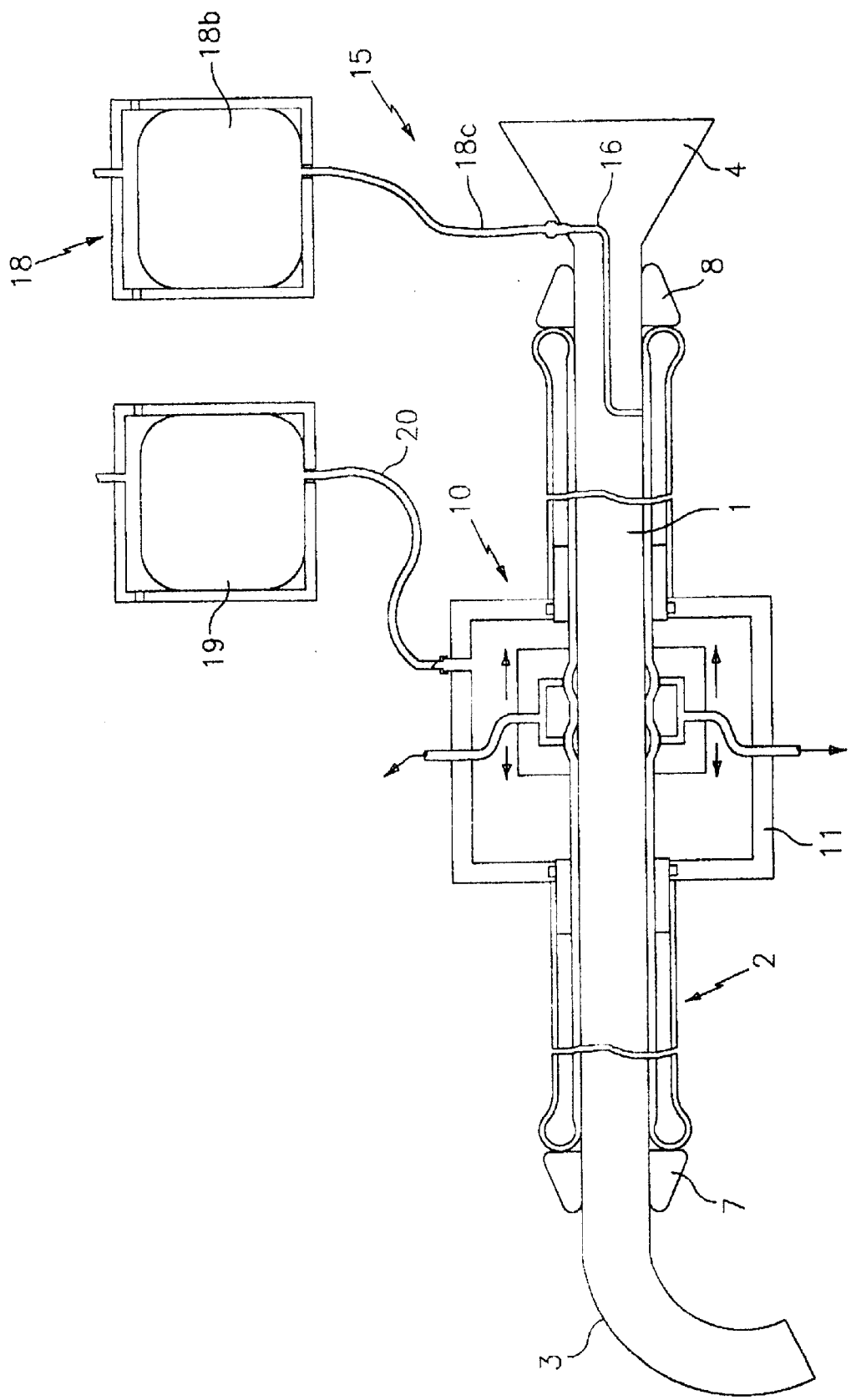
FIG. 7 is a trocar-invertible hose system according to a third preferred configuration example of the invention.

According to FIG. 7, the driving device of the third configuration example consists of a drive housing 11, which is located around the hose guidance bushing 5 like in the first and the second configuration example, and in which at least two vacuum grippers can alternately move in the axial direction of the trocar shaft 1. The vacuum grippers consist of small blocks with suction cups which penetrate through the openings in the drive bushing 5 and make tight contact with the inner invertible hose section 2*a*; the suction cups are located on the small block side that contacts the hose 2*a* and are provided with negative pressure by a vacuum pump to adhere to the hose material in the area of the inner invertible hose section 2*a*, providing a strong form-fitting connection to the inner hose section 2*a*. To that end the vacuum pump (not illustrated) is connected to a vacuum connector located in the housing 11 of driving device 10, which is connected to the suction cups through channels inside the small blocks. The movement of the small blocks is provided by a moving mechanism not shown in detail, and the production of the negative pressure within the suction cups is controlled so that the small blocks can continuously and alternately move back and forth, or in uniform steps with more than two small blocks, in a corresponding synchronous suction and release of the inner invertible hose section 2a, thereby producing a quasi continuous and uniform forward movement of the invertible hose 2.

As can easily be seen in FIG. 7, the vacuum in the suction cups lifts the inner invertible hose section 2a slightly from the trocar shaft. The forward motion of the trocar shaft 1 in this configuration example essentially occurs like in the previous configurations. As with the first and second configuration example, the entire arrangement is filled with a lubricant which takes over the lubrication of the invertible hose 2.

Figure 8:
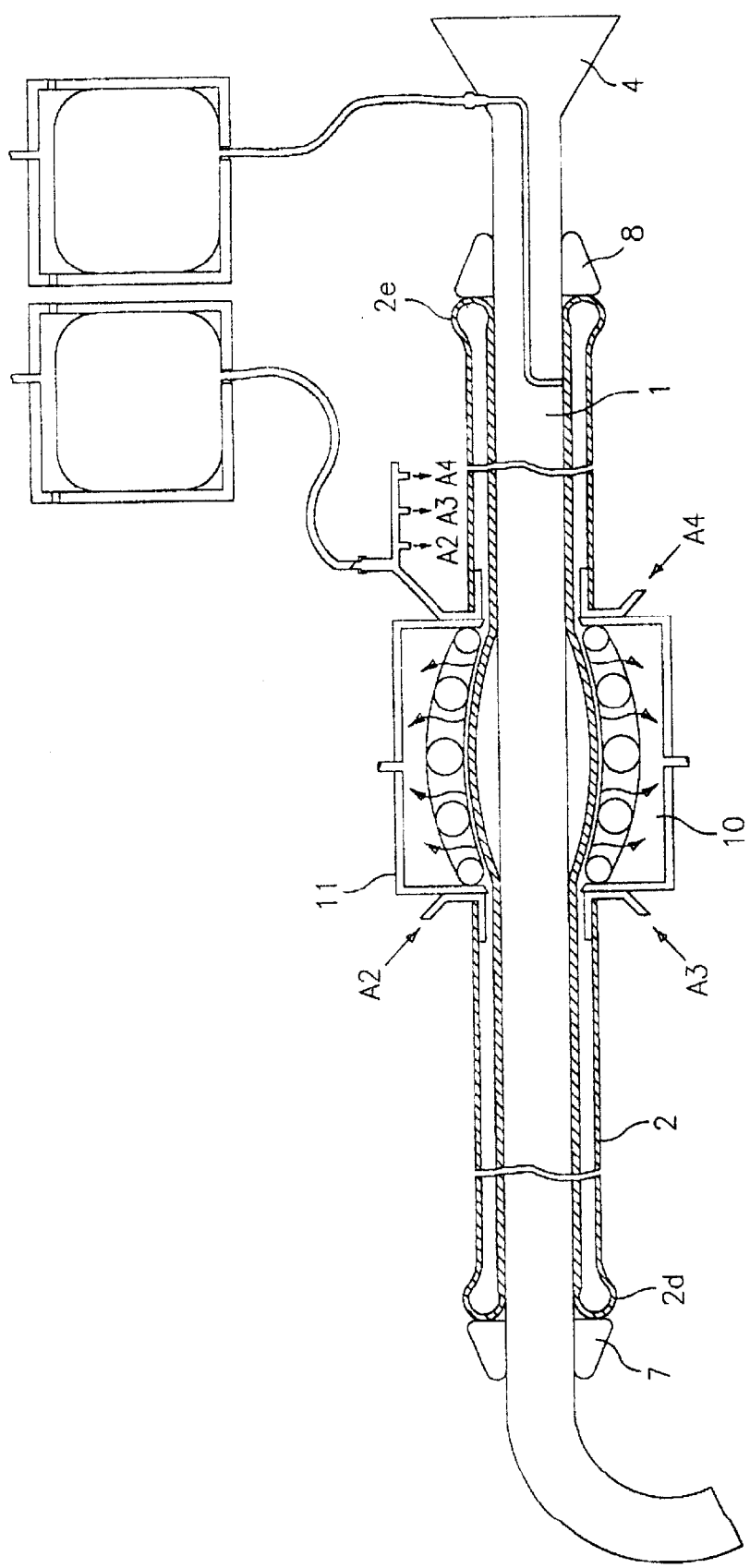
FIG. 8 is an alternative variation of the third configuration example.

FIG. 8 shows an alternative design of the third configuration example, where negative pressure produces a driving force on the invertible hose.

As can be seen in FIG. 8, the invertible hose 2 is turned up on both sides and together with a housing 11 of the drive mechanism forms a single unit without a driving bushing. I.e. in this configuration example the free ends of the external front and rear hose sections 2b and 2c are directly attached and seal the side walls of the drive housing 11.

The drive mechanism of the third configuration example is formed by a kind of caterpillar drive consisting of at least one elastic endless band, which is tensioned and driven by at least two wheels separated from each other in the forward movement direction. The entire driving device is located in the airtight housing, which is preferably made of two parts in the lengthwise direction and has a vacuum connector. The endless band surface has a number of openings or a perforation. A hose line links the vacuum connector to a not illustrated vacuum pump.

The housing 11 itself is open on the side facing the inner hose section 2a, where the endless band is routed so that it seals the open side of the housing 11 as tightly as possible. Gaps between the lateral edges of the endless band and the housing 11 can be sealed with suitable sealing lips attached to the housing walls, which allow the endless band to glide. Furthermore and in regard to the invertible hose 2 attached thereto, the housing 11 is designed so that the side of the endless band exposed to the outside forms a small gap or space above the inner hose section 2a.

During operation of this device, the inner space of the housing 11 is evacuated by the vacuum pump, which draws air out through the perforation in the endless band. suction is simultaneously provided to the inner hose section 2a which seals the outside of the endless band. This seal of the perforation increases the negative pressure inside the housing so that the endless band curves inward due to its elasticity and moves the inner hose section 2a with it, as clearly shown in FIG. 8.

This measure holds the inner hose section 2a tightly against the endless band along its length and simultaneously separates it from the trocar shaft 1. The advance of the trocar shaft 1 thus essentially takes place through the forces applied by the endless band at the front of the inverted area 2d to the front clamping part 7 during a forward motion of the front of the outer hose section 2b, while the inner hose section 2a makes no contact, particularly in the area of the driving unit. Because of the low friction the required advancing force on the front clamping part 7 is relatively low, so that no scaling (formation of folds) must be considered. As with the first and the second configuration example, a lubricant is pressed into the annular gap 9 which further reduces friction, especially in the area of the front and rear sealing bead 2d, 2e.

As with the first and the second configuration example, the third example as well as its alternative variations therefore provide a continuously or quasi continuously operating drive mechanism which has a mechanical effect on the invertible hose 2 and ensures a precisely controllable advance of the trocar.

In summary, the invention concerns a flexible trocar for a minimally invasive operation of the colon along its entire length from the anus. The flexible trocar consists of the external jacket 32 and internal jacket 33. All supply or function lines run in the space or annular gap between them. This includes the Bowden cables 37 for adjusting the distal end 3 of the trocar 1, and lines for optics, illumination, flushing with a liquid, flushing with air, $CO_2$ or similar, and lubrication. The inside diameter of the internal tube 33 is large enough so that at least one or several surgical instruments can be guided to the operating area for a minimally invasive operation. The trocar 1 is inserted into the intestine through an invertible hose system. The hose is driven by a number of friction wheels, suction cups or caterpillars acting on an inner hose section to drive the system in a continuous motion. Each of the inverted front and rear areas forms a bead which abuts tightly against the trocar 1 and seals the gap 9 between the trocar 1 and the inner hose section.

Lubricant is provided into the gap 9 between the trocar 1 and the inner hose section through an essentially radial hole in the external jacket of the invertible hose area, which is either connected by a function line to an external supply line, or via the rear clamping part by a lubricant injection spout which is adapted to the external jacket surface.

What is claimed is:

1. A flexible surgical trocar assembly having opposite proximal and distal ends, said trocar assembly comprising:

a) an outer flexible tubular jacket having a through bore which extends from said proximal end to said distal end of said trocar assembly, said outer flexible jacket forming an outer side wall on said trocar assembly;

b) an inner flexible jacket, said inner flexible jacket having a through bore which extends from said proximal end to said distal end of said trocar assembly, said inner flexible jacket being disposed in said through bore of said outer flexible jacket, said outer and inner flexible jackets combining to form an intervening annular space which extends from said proximal end to said distal end of said trocar assembly;

c) a plurality of surgical instrumentalities disposed in said annular space, at least some of said surgical instrumentalities extending from said proximal end to said distal end of said trocar assembly;

d) an invertible drive tube disposed about said outer flexible jacket, said invertible drive tube including a proximal inversion end, a distal inversion end, an inner wall which contacts said outer flexible jacket, and an outer wall which is outwardly spaced from said inner wall;

e) a distal clamping collar which is fixed to said outer flexible jacket and which is contacted by said distal inversion end of said invertible drive tube;

f) a proximal clamping collar which is fixed to said outer flexible jacket and which is contacted by said proximal inversion end of said invertible drive tube; and g) a drive mechanism contacting said inner wall of said invertible drive tube, said drive mechanism being selectively operable to move said inner wall of said invertible drive tube in the distal direction, or in the proximal direction, whereby said distal inversion and said proximal inversion ends of said invertible drive tube are selectively moved against said distal or proximal clamping collars, respectively, so as to selectively move the flexible jackets in the distal and proximal directions.

2. The trocar assembly of claim 1 further comprising first means for supplying a lubricant to an area of contact between said invertible tube and said outer flexible jacket.

3. The trocar assembly of claim 2 further comprising second means for supplying a lubricant to an area between said inner and outer walls of said invertible tube.

4. The trocar assembly of claim 2 wherein said drive assembly includes friction rollers which contact said inner wall of said invertible tube.

5. The trocar assembly of claim 2 wherein said drive assembly includes a movable endless belt which contacts said inner wall of said invertible tube.

6. The trocar assembly of claim 5 wherein said endless belt is perforated.

7. The trocar assembly of claim 6 wherein said endless belt is disposed in a sealed housing which can be selectively evacuated so as to cause said inner wall of said invertible tube to be pulled against and gripped by said endless belt.

8. The trocar assembly of claim 2 wherein said drive assembly includes at least one reciprocally movable suction cup which can selectively grip said inner wall of said invertible tube.

9. The trocar assembly of claim 8 wherein said suction cup is evacuated to grip said inner wall of said invertible tube during invertible tube-driving movement of said suction cup, and is devacuated to release said inner wall of said invertible tube during invertible tube non-driving movement of said suction cup.

* * * * *